(12) United States Patent
Ziegler

(10) Patent No.: US 7,894,572 B2
(45) Date of Patent: Feb. 22, 2011

(54) MULTI-TUBE IMAGING SYSTEM RECONSTRUCTION

(75) Inventor: Andy Ziegler, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 127 days.

(21) Appl. No.: 12/302,100

(22) PCT Filed: May 9, 2007

(86) PCT No.: PCT/US2007/068538

§ 371 (c)(1),
(2), (4) Date: Nov. 24, 2008

(87) PCT Pub. No.: WO2007/140093

PCT Pub. Date: Dec. 6, 2007

(65) Prior Publication Data

US 2009/0116612 A1 May 7, 2009

Related U.S. Application Data

(60) Provisional application No. 60/803,257, filed on May 26, 2006.

(51) Int. Cl.
*A61B 6/00* (2006.01)
(52) U.S. Cl. .............................................. 378/9; 378/8
(58) Field of Classification Search .................. 378/4, 378/8, 9
See application file for complete search history.

(56) References Cited

U.S. PATENT DOCUMENTS

| 4,637,040 | A | 1/1987 | Sohval et al. | |
|---|---|---|---|---|
| 4,991,190 | A | 2/1991 | Mori | |
| 5,173,852 | A | 12/1992 | Lonn | |
| 5,265,142 | A | 11/1993 | Hsieh | |
| 5,590,164 | A * | 12/1996 | Kawai et al. | 378/4 |
| 5,966,422 | A * | 10/1999 | Dafni et al. | 378/9 |
| 6,208,706 | B1 | 3/2001 | Campbell et al. | |
| 6,256,369 | B1 * | 7/2001 | Lai | 378/14 |
| 6,421,412 | B1 * | 7/2002 | Hsieh et al. | 378/9 |
| 6,483,890 | B1 | 11/2002 | Malamud | |
| 6,947,516 | B2 | 9/2005 | Okumura et al. | |
| 2004/0066906 | A1 * | 4/2004 | Hornegger et al. | 378/197 |
| 2004/0079232 | A1 | 4/2004 | Groh et al. | |
| 2004/0114710 | A1 | 6/2004 | Ozaki | |
| 2004/0213371 | A1 | 10/2004 | Bruder et al. | |
| 2005/0100127 | A1 | 5/2005 | Zhao et al. | |
| 2006/0193430 | A1 * | 8/2006 | Kuhn | 378/9 |
| 2007/0081622 | A1 * | 4/2007 | Bruder et al. | 378/7 |
| 2009/0279659 | A1 * | 11/2009 | David et al. | 378/7 |

FOREIGN PATENT DOCUMENTS

JP 2005177260 A 7/2005

* cited by examiner

*Primary Examiner*—Edward J Glick
*Assistant Examiner*—Alexander H Taningco

(57) ABSTRACT

A tomographic apparatus (10) includes at least two x-ray sources (14) that rotate about and alternately emit radiation into an imaging region (22). The at least two x-ray sources (14) emit radiation from a first set of angular positions during a first data acquisition cycle and from a different set of angular positions during a subsequent data acquisition cycle. At least two sets of detectors (24) detect primary radiation emitted by a corresponding one of the at least two x-ray sources (14) and produce data representative of the detected radiation. An interleaver (32) interleaves the data associated with the first and the subsequent data acquisition cycles for each of the at least two x-ray sources (14).

20 Claims, 3 Drawing Sheets

MULTI-TUBE IMAGING SYSTEM RECONSTRUCTION

CROSS REFERENCE TO RELATED APPLICATIONS

This application claims the benefit of U.S. provisional application Ser. No. 60/803,257 filed May 26, 2006, which is incorporated herein by reference.

The following relates to medical imaging systems. It finds particular application to computed tomography (CT) and, more particularly to data acquisition and reconstruction techniques.

The x-ray tubes in a conventional dual x-ray tube CT imaging system typically are driven concurrently or alternately while scanning a subject. When concurrently driven, both tubes emit radiation at the same time for at least a portion of the scan. During these periods of simultaneous emission, a detector detecting primary radiation from one of the tubes also detects cross scatter radiation associated with the other tube. The detection of the cross scatter radiation increases the total amount of scatter radiation detected by each detector. A higher scatter contribution generally leads to artifact and can reduce the visibility of halved temporal resolution.

With alternately driven x-ray tubes, each tube switches "on" and "off" such that only one of the tubes is emitting radiation at any given time. Such switching mitigates detection of cross scatter radiation by a detector detecting primary radiation since the other x-ray tube is not emitting radiation. However, alternately switching each tube also results in each tube emitting radiation for about half of the time relative to continuously driving (or not switching) each tube during data acquisition. As a result, the angular sampling of each x-ray tube decreases relative to the angular sampling achieved with continuously driven x-ray tubes. This may decrease the visibility of the halved temporal resolution due to a lower spatial resolution of the reconstruction.

In view of the above, there is an unresolved need for systems and/or methods that overcome these and/or other deficiencies with conventional multi-tube systems.

Aspects of the present invention address these matters, and others.

According to one aspect, a tomographic apparatus is illustrated. The tomographic apparatus includes at least two x-ray sources that rotate about and alternately emit radiation into an imaging region. The at least two x-ray sources emit radiation from a first set of angular positions during a first data acquisition cycle and from a different set of angular positions during a subsequent data acquisition cycle. At least two sets of detectors detect primary radiation emitted by a corresponding one of the at least two x-ray sources and produce data representative of the detected radiation. An interleaver interleaves the data associated with the first and the subsequent data acquisition cycles for each of the at least two x-ray sources.

Figure 1:
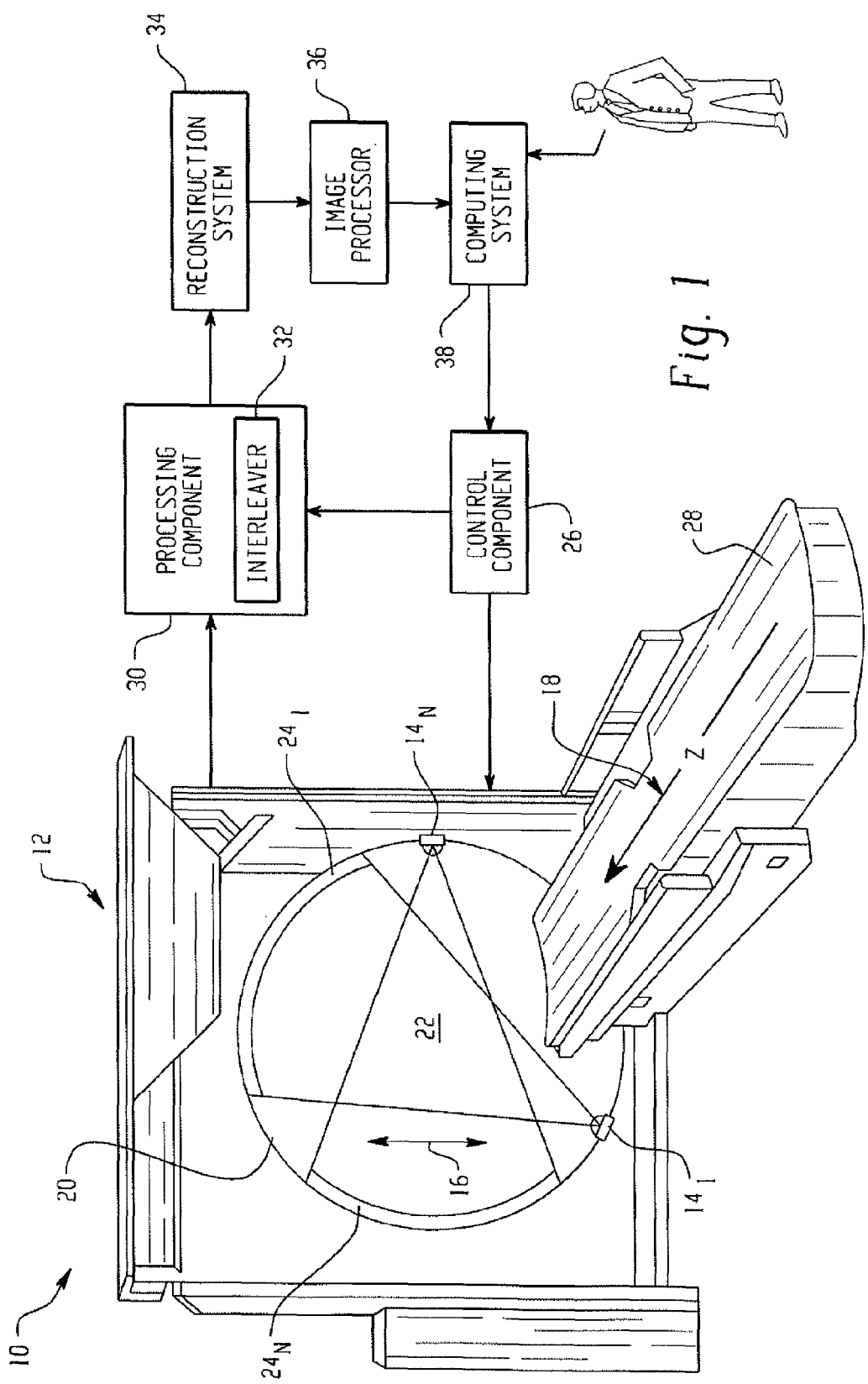
FIG. 1 illustrates an exemplary medical imaging system with a plurality of x-ray sources.

With reference to FIG. 1, a medical imaging system 10 is illustrated. The medical imaging system 10 includes multiple x-ray sources that are alternately driven and detectors that detect primary radiation during one or more data acquisition cycles (e.g., revolutions or partial revolutions of the x-ray sources about an imaging region). In one instance, radiation detected in two or more of the data acquisition cycles is used to form a data set for reconstruction. For example, the data associated with two or more of the data acquisition cycles (the entire data sets or subsets thereof) can be interleaved or otherwise combined to form the data set. In this instance, the data acquired in a subsequent data acquisition cycle(s) can be acquired at different angular locations (e.g., shifted by an angular increment) from a previous cycle such that the data detected during the subsequent cycle(s) includes angular samples that were not acquired in the previous cycle(s). The resultant data set may include higher angular sampling relative to the angular sampling associated with any of the individual data acquisition cycles.

The medical imaging system 10 includes a scanner 12 having N x-ray sources $14_1$, $14_N$ (collectively referred to herein as x-ray sources 14), wherein N is an integer equal to or greater than one. The x-ray sources 14 are positioned at an angular offset (e.g., 90, 120, etc. degrees) with respect to each other within an axial or transverse plane 16 that is orthogonal to a longitudinal or z-axis 18. In one instance, the x-ray sources 14 are disposed about a rotating gantry 20. As such, rotating the gantry 20 about an imaging region 22 rotates the x-ray sources 14 about the imaging region 22. In another instance, the x-ray sources 14 are rotated about the imaging region 22 via other techniques such as electronically deflecting the x-ray beam. During scanning, the x-ray sources 14 can be alternately driven such that only one of the x-ray sources 14 is emitting radiation into the imaging region 22 at any moment in time.

The scanner 12 further includes N sets of detectors $24_1$, $24_N$ (collectively referred to herein as detectors 24). Each set of the detectors 24 subtends an angular arc opposite one of the x-ray sources 14 to define the imaging region 22 therebetween. In one instance, each detector within each set of detectors 24 rotates with and corresponds to a particular one of the x-ray sources 14 (e.g., with a third generation system). In another instance the detectors within each set of detectors 24 reside at fixed locations and, at any moment in time, are determined by the angular position of the x-ray source 14 (e.g., with a fourth generation system). Each set of detectors 24 detects primary radiation when a corresponding one of the x-ray source 14 emits radiation.

A subject (or patient) support 28 supports a subject such as a human within an imaging region 22. The support 28 may be movable in order to allow an operator to guide the subject to a suitable location within the imaging region 22 before, during and/or after performing a helical, axial, and/or other scan, for example, by moving the support 28 along the z-axis 18.

A control component 26 controls each of the x-ray sources 14. In one instance, such control includes alternately switching each of the x-ray sources 14 "on" and "off" such that the x-ray sources 14 alternately emit radiation into the imaging region 22. Such control includes driving each of the x-ray sources 14 with a suitable duty cycle and/or switching frequency that determines which and when each of the x-ray sources 14 emits radiation during each angular sampling interval for each data acquisition cycle. This can include determining the angular position of the x-ray sources 14 at which data is sampled. In some instances, this includes determining an angular increment for each data acquisition cycle that shifts the angular position of the x-ray sources 14 by an angular offset so that data detected during a subsequent cycle includes angular samples that were not acquired in a previous cycle.

By way of non-limiting example, in a first data acquisition cycle the control component 26 may alternately switch the x-ray sources 14 "on" and "off" such that the x-ray source $14_1$ emits radiation during a first portion of the switching period and the x-ray source $14_N$ emits radiation during a second portion of the switching period. In this example, the x-ray source $14_1$ does not emit radiation during the second portion of the switching period and the x-ray source $14_N$ does not emit radiation during the first portion of the switching period. As a result, primary radiation can be detected by acquiring data with the detectors opposite the active x-ray source 14. In a subsequent data acquisition cycle, the angular positioning of the x-rays 14 can be shifted by the angular increment to capture samples that were not sampled during the first data acquisition cycle. Upon such shifting, the x-ray source $14_N$ now emits radiation during the first portion of the switching period and the x-ray source $14_1$ emits radiation during the second portion of the switching period. As a result, the primary radiation detected in the subsequent data acquisition cycle for each of the x-ray sources 14 includes samples that were not detected during the previous data acquisition cycle.

Each of the detectors 24 produces a signal indicative of the detected primary radiation. A processing component 30 processes at least a portion of these signals. In one instance, the processing component 30 includes an interleaver 32 that interleaves data acquired during different data acquisition cycles. For examples, for each of the sources 14 the interleaver 32 can combine data collected during one or more cycles by interleaving the data from the different cycles. In one instance, the resultant data set created by such interleaving includes greater angular sampling relative to the angular sampling of any individual data acquisition cycle. Various techniques can be used to determine which data from which cycles to use to form a data set for reconstruction.

By way of example, with cardiac gated CT reconstruction can be performed in a single cycle mode in which data acquired during at least part of a single rotation or revolution of the x-ray sources 14 is reconstructed. Data collected during one or more other data acquisition cycles can also be used in this reconstruction. A suitable approach for determining which data from which data acquisition cycles to use includes defining a phase point within a cardiac phase and a window about the phase point. With this approach, data is selected from the different cycles based on the phase point and the window. For example, the phase point may represent a quiet phase of a cardiac cycle in an angular range. The window width about the phase point can be set to collect enough data around the set point to form a desired data set for reconstruction. For example, the width can be set to capture enough data for a 180 degree retrospective cardiac reconstruction. This width may be set to capture a minimal amount of data (180 degrees plus a source angle) for the reconstruction. In another instance, the window width is set to capture additional overlapping data that can be combined to reduce motion artifact.

The processed data is provided to a reconstruction system 34, which reconstructs the data to generate volumetric data indicative of the scanned region of the subject. As described above, this data may include data acquired at different angular sampling locations during different data acquisition cycles that was interleaved. An image processor 36 processes the volumetric image data generated by the reconstruction system 34. The generated images can then be displayed, filmed, archived, forwarded to a treating clinician (e.g., emailed, etc.), fused with images from other imaging modalities, further processed (e.g., via measurement and/or visualization utilities and/or a dedicated visualization system), stored, etc.

A computing system (or console) 38 facilitates operator interaction with and/or control of the scanner 12. Software applications executed by the computing system 34 allow the operator to configure and/or control operation of the scanner 12. For instance, the operator can interact with the computing system 38 to select scan protocols, initiate, pause and terminate scanning, view images, manipulating volumetric image data, measure various characteristics of the data (e.g., CT number, noise, etc.), etc. The computing system 38 communicates various information to the control component 26, including, but not limited to, instructions and/or parameters such as x-ray tube voltage, current, switching patterns, duty cycle, data combining technique, etc. The control component 26 uses such information as described above to control the scanner 12.

Figure 2:
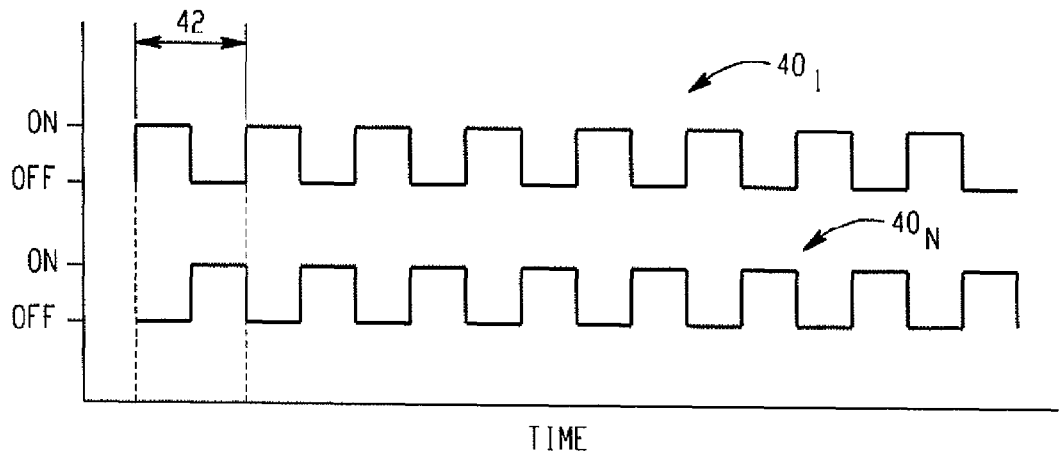
FIG. 2 illustrates exemplary switching patterns for alternately switching multiple x-ray sources during a data acquisition cycle.

FIG. 2 illustrates exemplary switching patterns for alternately switching the x-ray sources 14. For sake of brevity and clarity, only two such switching patterns $40_1$ and $40_N$ (collectively referred to herein as switching patterns 40) are shown. The switching pattern $40_1$ is used to switch one of the x-ray sources 14 (e.g., the x-ray source $14_1$) and the switching pattern $40_N$ is used to switch another of the x-ray source 14 (e.g., the x-ray source $14_N$). As depicted, during each period 42 the switching patterns 40 alternately toggle "on" and "off," which alternately switches the sources 14 switch "on" and "off" within each period 42. In this example, the switching patterns 40 include square pulses with about equal duty cycles. However, in other instance the duty cycles, the shapes of the pulses, the amplitudes of the pulses, etc. may be different.

Figure 3:
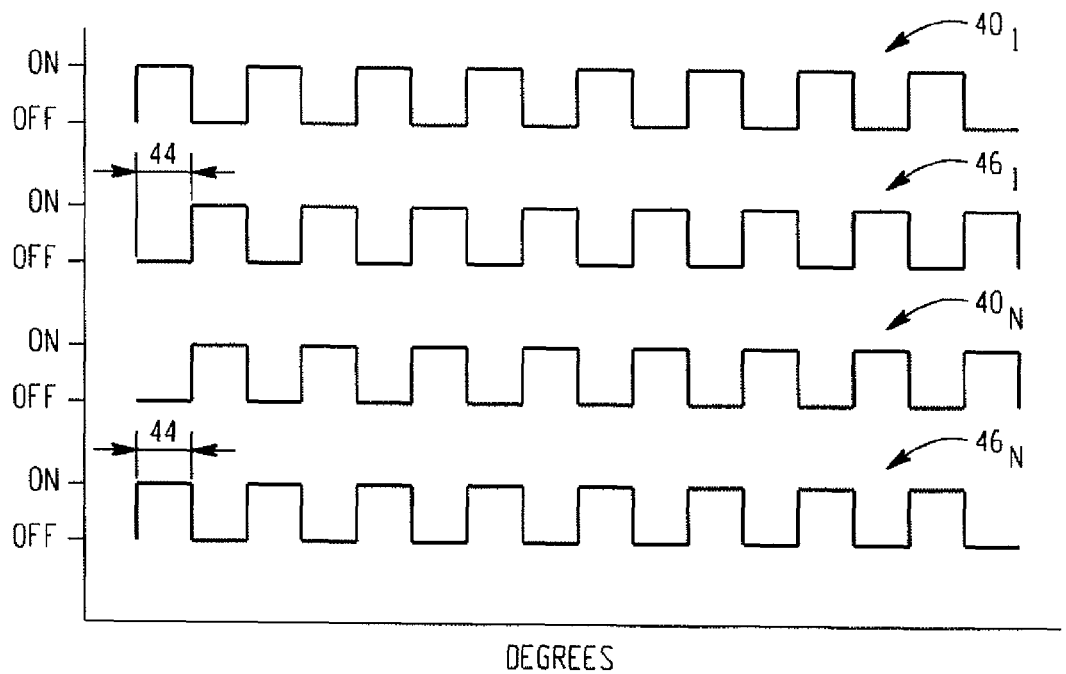
FIG. 3 illustrates exemplary shifted switching patterns for alternately switching multiple x-ray sources during a subsequent data acquisition cycle.

FIG. 3 illustrates exemplary shifted switching patterns for switching the x-ray sources 14 during a subsequent data acquisition cycle. As depicted, the initial switching patterns $40_1$ and $40_N$ are shifted by an angular increment 44 to render switching patterns $46_1$ and $46_N$. In this example, the angular increment 44 corresponds to an angular distance that will lead to the capture of angular samples in the subsequent cycle that were not sampled in previous cycle. In one instance, the angular increment 44 is determined as a function of $$\frac{2\pi}{(K-0.5)},$$

wherein K is a number of angular samples. This approach can be used to determine the angular increment 44 for any number of x-ray sources 14 and any number of cycles. Other techniques for determining the angular increment 44 are also contemplated herein. For example, in an alternative approach the angular increment 44 can be set to render homogeneous angular sampling when combining data from multiple cycles.

Figure 4:
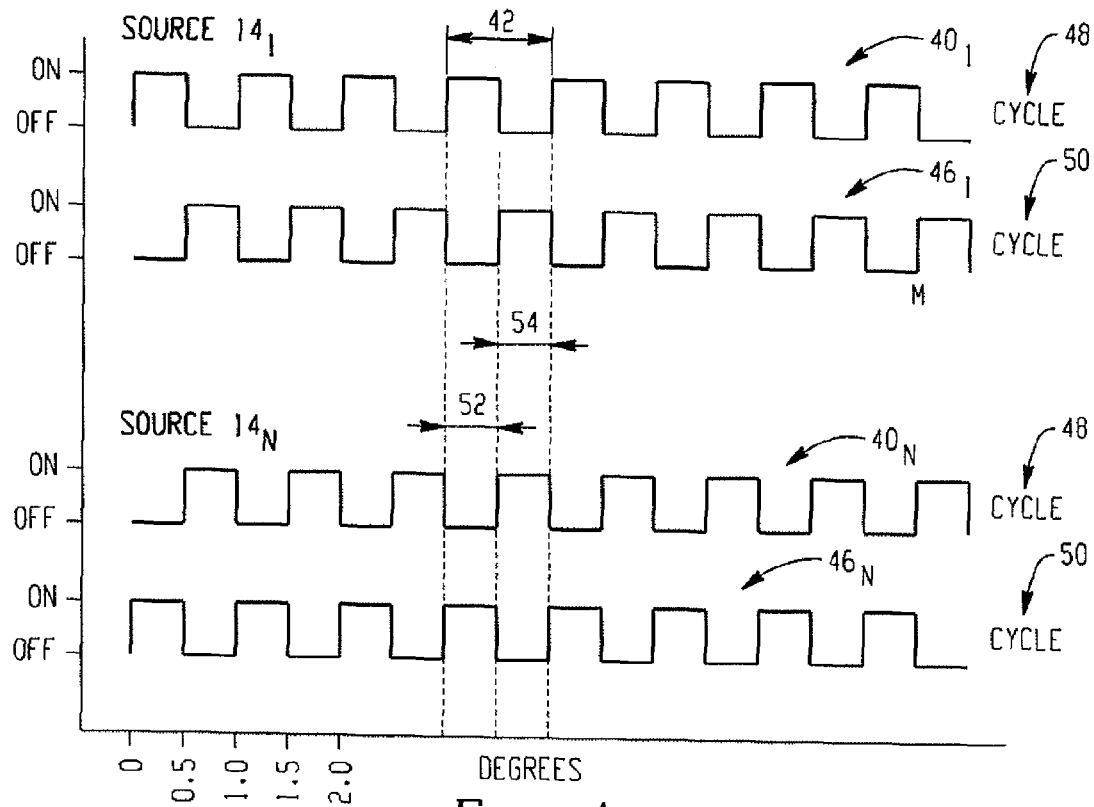
FIG. 4 illustrates alternately switched x-ray sources over multiple data acquisition cycles.

FIG. 4 provides an example in which the sources $14_1$, $14_N$ are respectively switched with the switching patterns $40_1$, $40_N$ during a first data acquisition cycle 48 and with the shifted switching patterns $46_1$, $46_N$ (shifted by the increment 44) during a second data acquisition cycle 50. As depicted, the source $14_1$ is switched via the switching pattern $40_1$ such that during the first cycle 48 radiation is emitted and data is collected during a first portion 52 of the sampling period 42. During the second cycle 50, the source $14_1$ is switched via the switching pattern $46_1$ such that radiation is emitted and data is collected during a second portion 54 of the sampling period 42. The source $14_N$ is switched via the switching pattern $40_N$ during the first cycle 48 such that radiation is emitted and data is collected during the second portion 54 of the sampling period 42 and via the switching pattern 46$_N$ such that radiation is emitted and data is collected during the first portion 52 of the sampling period 42.

In this non-limiting example, the angular increment is about 0.5 degrees. For instance, if each cycle 48, 50 represents a gantry revolution and the initial angle is 0 (or 360) degrees, the angular positions for the x-ray source 14$_1$ during the cycle 48 are 0, 1, 2, ..., and 359 and during the cycle 50 are 0.5, 1.5, 2.5, ..., 359.5. The angular positions for the x-ray source 14$_N$ during the cycle 48 are 0.5, 1.5, 2.5, ..., 359.5 and during the cycle 50 are 0, 1, 2, ..., and 359. In this example, the angular increment 44 corresponds to an angular distance that will lead to the capture of angular samples in the cycle 50 that were not sampled in the cycle 48 for both x-ray sources 14. It is to be appreciated that although the above example is described in connection with 360 degrees, in another instance the data may be collected in less than 360 degrees. For instance, for a 180 degree reconstruction data can be collected over 180 degrees plus a fan angle.

Figure 5:
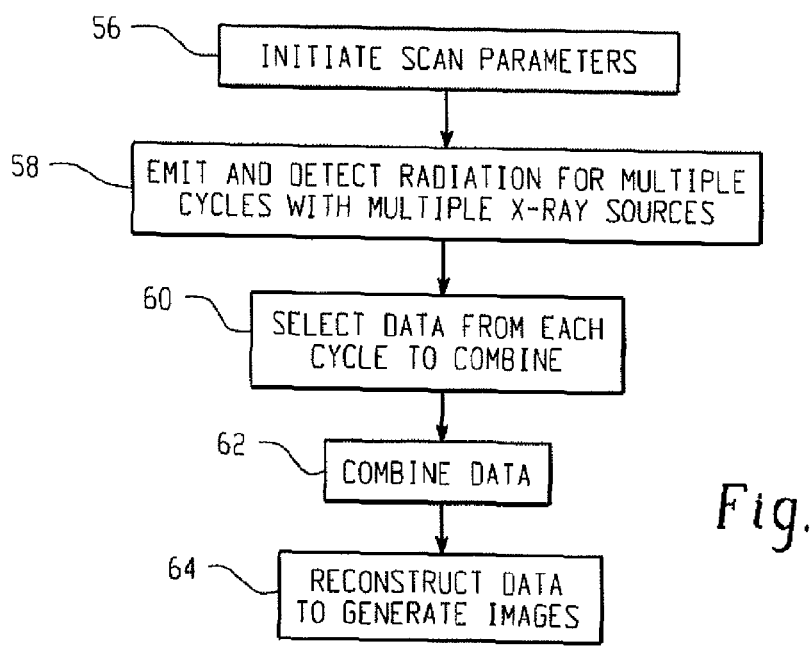
FIG. 5 illustrates an exemplary method for alternately switching multiple x-ray sources.

FIG. 5 illustrates a non-limiting method for scanning a subject with the medical imaging system 10. At reference numeral 56, scan parameters are initiated. This includes selecting a scan protocol and configuring the scanner 12 to scan a subject in the imaging region 22. This also include providing information such as the data combining technique, a phase point and a window width (for cardiac applications), a number of cycles to combine, etc. At reference numeral 58, the x-ray sources 14 are alternately driven and data is collected during one or more data acquisition cycles. When each x-ray source 14 is active, a corresponding set of the detectors 24 detects the primary radiation emitted by that source 14. In one instance, the angular increment 44 is used to offset the angular sampling for each x-ray source 14 for each cycle. The angular increment 44 can be set such that the samples acquired in a subsequent cycle represent samples that were not acquired in a previous cycle.

At 60, data from each of the cycles is selected to form a data set for reconstruction. As discussed previously, the data can be selected based on a phase point and a window width in order to retrieve a suitable amount of data, for example, for a 180 degree cardiac gated retrospective reconstruction. At 62, the selected data is combined to form the reconstruction data set. In one instance, this includes interleaving the data corresponding to each of the sources from the different acquisition cycles to form a single data set. By acquiring samples for during each cycle at different angular positions, the temporal resolution of the resultant data set can be increased. At 64, the reconstruction system 34 reconstructs the data to generate corresponding images.

The systems and/or methods described herein and/or derivations thereof can be applied in medical imaging applications such as, but not limited to, cardiac CT, small animal x-ray imaging, security scanning systems, non-destructive materials analysis or defect detection, machine vision, systems incorporating distributed sources, etc.

The invention has been described with reference to the preferred embodiments. Of course, modifications and alterations will occur to others upon reading and understanding the preceding description. It is intended that the invention be construed as including all such modifications and alterations insofar as they come within the scope of the appended claims.

The invention claimed is:

1. A tomographic apparatus comprising:

at least two x-ray sources that rotate about and alternately emit radiation into an imaging region, wherein the at least two x-ray sources emit radiation from a first set of angular positions during a first data acquisition cycle and from a different set of angular positions during a subsequent data acquisition cycle, wherein during the first data acquisition cycle a first of the two sources rotates around the image region and is turned on and off a plurality times and emits radiation at a first plurality of angles and a second of the two sources rotates around the image region and is turned on and off a plurality times and emits radiation at a second different plurality of angles, and, during the subsequent acquisition cycle the first of the two sources rotates around the image region and is turned on and off a plurality times and emits radiation at the second different plurality of angles and the second of the two sources rotates around the image region and is turned on and off a plurality times and emits radiation at the first plurality of angles;

at least two sets of detectors that each detect primary radiation emitted by a corresponding one of the at least two x-ray sources and produce data representative of the detected radiation; and an interleaver that selectively interleaves the data associated with the first and the subsequent data acquisition cycle to form a reconstruction data set.

2. The apparatus of claim 1 wherein samples collected during the first and the subsequent data acquisition cycle include different samples.

3. The apparatus of claim 1 wherein the set of angular positions associated with the subsequent data acquisition cycle includes the set of angular positions associated with the first data acquisition cycle offset by an angular increment.

4. The apparatus of claim 3 wherein the angular increment is a function of:

$$\frac{2\pi}{(K-0.5)},$$

wherein K is a number of angular samples.

5. The apparatus of claim 1 wherein the first and subsequent acquisition cycles correspond to different revolutions of both the at least two x-ray sources around the imaging region.

6. The apparatus of claim 1 wherein the interleaved data set includes higher angular sampling relative to the angular sampling associated with the first or the subsequent data acquisition cycles.

7. The apparatus of claim 1 wherein data associated with at least one additional data acquisition cycle and another different set of angular positions is interleaved with the data from the first and the subsequent data acquisition cycles to form the reconstruction data set.

8. The apparatus of claim 1 wherein the interleaved data includes data for a 180 degree retrospective gated cardiac reconstruction.

9. The apparatus of claim 1 wherein the interleaved data corresponds to data within a window around a phase point within a quiet phase of a cardiac cycle.

10. The apparatus of claim 1 further including a reconstruction system that reconstructs the interleaved data to generate an image of a subject within the imaging region.

11. The apparatus of claim 1 wherein each of the at two x-ray sources is switched as a function of a switching pattern.

12. The apparatus of claim 11 wherein each switching pattern alternately turns a corresponding one of the at least two x-rays sources "on" and "off" during different portions of a sampling period.

13. A computed tomography reconstruction method comprising:

alternately driving at least two x-ray sources to alternately emit radiation into an imaging region from a first set of angular positions during a first data acquisition cycle and from different sets of angular positions during a subsequent data acquisition cycle, wherein during the first data acquisition cycle a first of the two sources rotates around the image region and is turned on and off a plurality times and emits radiation at a first plurality of angles and a second of the two sources rotates around the image region and is turned on and off a plurality times and emits radiation at a second different plurality of angles, and, during the subsequent acquisition cycle the first of the two sources rotates around the image region and is turned on and off a plurality times and emits radiation at the second different plurality of angles and the second of the two sources rotates around the image region and is turned on and off a plurality times and emits radiation at the first plurality of angles;

detecting, respectively by at least two different detector arrays, primary radiation emitted by the at least two x-ray sources at each of the angular positions for each of the data acquisition cycles; and combining data indicative of the detected primary radiation from the data acquisition cycles to form a reconstruction data set.

14. The method of claim 13 further including incrementing the angular positions for each subsequent data acquisition cycle by an angular increment to capture a different set of samples in each subsequent data acquisition cycle.

15. The method of claim 13 wherein the angular increment is determined by $$\frac{2\pi}{(K-0.5)},$$

wherein K is a number of angular samples.

16. The method of claim 13 wherein the first and subsequent data acquisition cycles correspond to different rotations of the at least two x-ray tubes around the imaging region.

17. The method of claim 13 further including interleaving the data to form a data set with a higher angular sampling relative to the angular sampling associated with any one data acquisition cycle.

18. The method of claim 13 wherein the primary radiation is detected during a gated cardiac scan.

19. The method of claim 13, wherein the at least two different sources are at least two different x-ray tubes.

20. An apparatus comprising:

means for alternately emitting radiation into an imaging region during two or more data acquisition cycles at different angular locations for each of the two or more data acquisition cycles, wherein during the first data acquisition cycle a first of two sources rotates around the image region and is turned on and off a plurality times and emits radiation at a first plurality of angles and a second of the two sources rotates around the image region and is turned on and off a plurality times and emits radiation at a second different plurality of angles, and, during the subsequent acquisition cycle the first of the two sources rotates around the image region and is turned on and off a plurality times and emits radiation at the second different plurality of angles and the second of the two sources rotates around the image region and is turned on and off a plurality times and emits radiation at the first plurality of angles;

means for detecting primary radiation traversing the imaging region and producing data indicative of the detected primary radiation;

means for selecting data associated with each of the two or more data acquisition cycles; and means for combining the selected data to form a reconstruction data set with a desired angular sampling.

* * * * *